United States Patent
Reddy et al.

(10) Patent No.: US 7,824,690 B1
(45) Date of Patent: *Nov. 2, 2010

(54) MAREK'S DISEASE VIRUS VACCINE

(75) Inventors: Sanjay M. Reddy, College Station, TX (US); Blanca M. Lupiani, College Station, TX (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 187 days.

This patent is subject to a terminal disclaimer.

(21) Appl. No.: 11/800,475

(22) Filed: May 4, 2007

Related U.S. Application Data

(63) Continuation of application No. 10/430,773, filed on May 6, 2003, now Pat. No. 7,214,524.

(51) Int. Cl.
*A61K 39/255* (2006.01)
*C12N 7/00* (2006.01)

(52) U.S. Cl. .............. 424/205.1; 424/229.1; 435/69.1; 435/235.1

(58) Field of Classification Search .................... None
See application file for complete search history.

(56) References Cited

PUBLICATIONS

Rispens et al. Avian Diseases. 1972; 16: 108-125.*
Lee et al. Journal of Veterinary Medical Science. 2000; 62 (3): 287-292.*
Chang et al. Journal of Veterinary Medical Science. 2002; 64 (12): 1091-1095.*
Witter. Poultry Science. 1998; 77 (8): 1197-203.*
Morgan, Robin W., et al, "Marek's Disease Virus gC and meq Mutants with Dramatic Reductions in Tumour Incidences and Horizontal Transmission", Avian Pathology, vol. 27, Supplement 1, Apr. 1998, Proceedings of an International Symposium held to honour Dr. L.N. Payne.
Morgan, Robin, et al., "Clues to MDV Oncogenicity: MEQ Mutants and Molecular Differences Among MDV Serotype1 Isolates", 2nd International Workshop on Molecular Pathogenesis of MDV, Aug. 8-11, 1998.

* cited by examiner

*Primary Examiner*—Mary E Mosher
*Assistant Examiner*—Myron G Hill
(74) *Attorney, Agent, or Firm*—John D. Fado; Randall E. Deck; Lesley Shaw

(57) ABSTRACT

An effective vaccine for Marek's disease may be prepared using a viral agent which is a Marek's disease virus unable to express a functional meq protein. This viral agent is effective to elicit an immune response in a chicken to very virulent strains of Marek's disease virus without causing a significant degree of pathogenicity in the inoculated bird. Suitable formulations of the vaccine for use in chickens include an effective immunization dosage of this novel viral agent with a pharmaceutically acceptable carrier or diluent.

7 Claims, 2 Drawing Sheets

MAREK'S DISEASE VIRUS VACCINE

BACKGROUND OF THE INVENTION

1. Field of the Invention

The invention relates to novel vaccines for protecting chickens against infection with Marek's disease virus.

2. Description of the Prior Art

Marek's disease (MD), a highly prevalent and important lymphoproliferative disease of chickens, is controlled in commercial chickens by live virus vaccines consisting of attenuated or naturally avirulent MD-related herpesviruses. Although vaccination programs have been considered highly effective overall, the poultry industry continues to experience losses due to MD. Given the tendency of MD virus to become more virulent with time coupled with the economic pressures confronting the poultry industry, there is still a strong incentive to develop even more efficacious products that will protect better in the face of early challenge with very virulent field strains without causing adverse side effects. This invention relates to a novel vaccine against MD which does in fact provide superior protection and improved safety compared to certain existing commercial vaccines.

There are three distinct serotypes of MD virus found in chickens: (1) serotype 1, the oncogenic form responsible for the disease, including high- and low-virulence MD virus and their attenuated variants; (2) serotype 2, a nononcogenic MD virus; and (3) serotype 3, herpesvirus of turkeys (HVT).

The prototype MD vaccine consists of the serotype 3 virus originally isolated from turkeys as reported in Witter et al. [Am. J. Vet. Res. 31: 525-538 (1970)] and Okazaki et al. [U.S. Pat. No. 3,642,574]. Its lack of oncogenicity, self-limiting infection, good replication in vivo and in vitro, availability as cell-free and cell-associated preparations, and high protective efficacy have established HVT as a standard for MD vaccines throughout the world. A commonly used strain of HVT is FC126.

Vaccines produced from the naturally avirulent SB-1 strain [Schat et al., J. Natl. Cancer Inst. 60: 1075-1082 (1978) and U.S. Pat. No. 4,160,024], an isolate of a serotype 2 MD virus, have been licensed in the United States since 1984. The SB-1 strain is poorly protective against the highly virulent MDV strains. It is usually used in combination with HVT as a bivalent vaccine since the two viruses together produce greater protection than does either one alone [Schat et al., Avian Pathol. 11: 593-606 (1982); Witter, Avian Pathol. 11: 49-62 (1982), herein incorporated by reference]. This phenomenon has been termed "protective synergism". The SB-1+HVT bivalent vaccine represents about 18% of the United States market for MD vaccines at present and is considered to be among the most efficacious of the various MD products available. However, sporadic losses occur despite its use.

Another MD vaccine produced from strain CVI988 clone C (CVI988/C) has been licensed for commercial use in the United States. This vaccine was derived from a mildly virulent serotype 1 MD virus attenuated by serial passage in tissue culture and has been reported by deBoer et al. [Avian Dis. 30: 276-283 (1986)]. A further passaged derivative of CVI988/C, identified as CVI988/C/R6, has also been described by de Boer et al. [Advances in Marek's Disease Research, pp. 405-413 (1988)]. More recently, the original low-passage strain, designated CVI988/Rispens, which has been in commercial use in other countries for a number of years, was found to be highly effective against challenge with several very virulent MD virus strains by Witter et al. [4th Int'l Symp. Marek's Disease, pp. 315-319 (1992)].

An experimental vaccine derived from Md11, a very virulent serotype 1 MD field isolate, was reported by Witter, supra. Md11 was attenuated by 75 serial passages in cell culture, and the resultant vaccine designated Md11/75C. This vaccine has been shown to provide good protection against challenge with Md5 and most other highly virulent MD viruses tested; but it was less efficacious against challenge with the JM/102W strain, a prototype MD virus effectively protected against by HVT and SB-1 vaccines. Furthermore, its efficacy was consistently lower in chicks with HVT antibody.

In U.S. Pat. No. 4,895,717, Witter disclosed a revertant derivative of Md11/75C which was referred to as Md11/75C/R2. Md11/75C/R2 was shown to be superior to several other monovalent vaccines and was the equal of a bivalent (HVT+SB-1) vaccine [Witter, Avian Dis. 31: 752-765 (1987)]. However, the inherent pathogenicity of serotype 1 viruses and the potential of attenuated strains to revert to greater pathogenicity (Witter et al., Avian Pathol. 13: 75-92 (1984)] are factors to be considered in the licensing of such products. A clone derived from further passages of the Md11/75C/R2 strain, designated Md11/75C/R2/23 (or R2/23), was found by Witter et al. [Avian Dis., 35:877-891 (1991)] to possess the highly protective nature of the parent strain without its residual pathogenicity.

Witter also described another MD vaccine derived from 301B/1, a nonpathogenic serotype 2 field isolate, in U.S. Pat. No. 4,895,718, the contents of which are incorporated by reference herein. Strain 301B/1 possessed superior replicative ability to SB-1, as well as greater protectivity against challenge to viruses.

Still other concerns have arisen over the use of some MD vaccines. As indicated, bivalent vaccines composed of MD virus serotypes 2 and 3 are currently widely used in the U.S. and have provided excellent protection against certain MD strains. However, use of such vaccines containing serotype 2 MD virus may lead to increased mortality from another disease, lymphoid leukosis. This enhancement of lymphoid leukosis in avian leukosis virus infected chickens resulting from vaccination with products containing serotype 2 MD virus has been an unfortunate deterrent to their expanded use.

Thus, although HVT, SB-1, CVI988, CVI988/C, Md11/75C, Md11/75C/R2 and 301B/1 are all effective against certain MD viruses, none of these vaccines protect optimally against all MD challenge viruses in all chickens. Moreover, these vaccines have exhibited reduced efficacy against some of the more recently isolated very virulent strains of MD virus. To avert any large-scale outbreaks of MD in the future, the need exists to develop improved vaccines effective against the very virulent strains of MD virus.

SUMMARY OF THE INVENTION

We have now discovered that an effective vaccine for Marek's disease may be prepared using a viral agent which is a Marek's disease virus unable to express a functional meq protein. This viral agent is effective to elicit an immune response in a chicken to very virulent strains of Marek's disease virus without causing a significant degree of pathogenicity in the inoculated bird. Suitable formulations of the vaccine for use in chickens include an effective immunization dosage of this novel viral agent with a pharmaceutically acceptable carrier or diluent.

In accordance with this discovery, it is an object of the invention to provide a novel, highly protective vaccine against MD in chickens.

It is also an object of the invention to provide a vaccine which provides greater protection against very virulent strains of Marek's disease virus than those vaccines presently in commercial use.

It is another object of the invention to improve the viability and productivity of chickens, particularly broilers and layers, and to reduce economic losses in the poultry industry caused by MD.

Other objects and advantages of this invention will become readily apparent from the ensuing description.

DEPOSIT OF BIOLOGICAL MATERIAL

Mutant Marek's disease virus clone Md5Δmeq has been deposited under the provisions of the Budapest Treaty in the American Type Culture Collection (ATCC), 10801 University Blvd., Manassass, Va., 20110-2209, USA, on Jan. 22, 2003, and has been assigned Accession No. ATCC PTA-4944.

DETAILED DESCRIPTION OF THE INVENTION

As used herein, "mutant" refers to any stable virus whose functional properties are different from the parent strain.

"Vaccine" is defined herein in its broad sense to refer to any type of biological agent in an administratable form capable of stimulating an immune response in an animal inoculated with the vaccine. For purposes of this invention, the vaccine may comprise either the virus itself or an immunogenic (antigenic) component of the virus. The vaccine may also be produced from a vector having inserted therein a gene which encodes an immunogenic component of the virus.

The present invention provides Marek's disease virus mutants which are unable to express functional (i.e., active) meq protein, and which are effective to elicit an immune response in a chicken to Marek's disease virus without causing a significant degree of pathogenicity in the chicken. As used herein "without causing a significant degree of pathogenicity" in the chicken is defined as no gross MD specific lesions being observable in the inoculated chicken, even in highly susceptible chicken lines, although a few type C MDV lesions may be seen upon microscopic examination.

Figure 1:
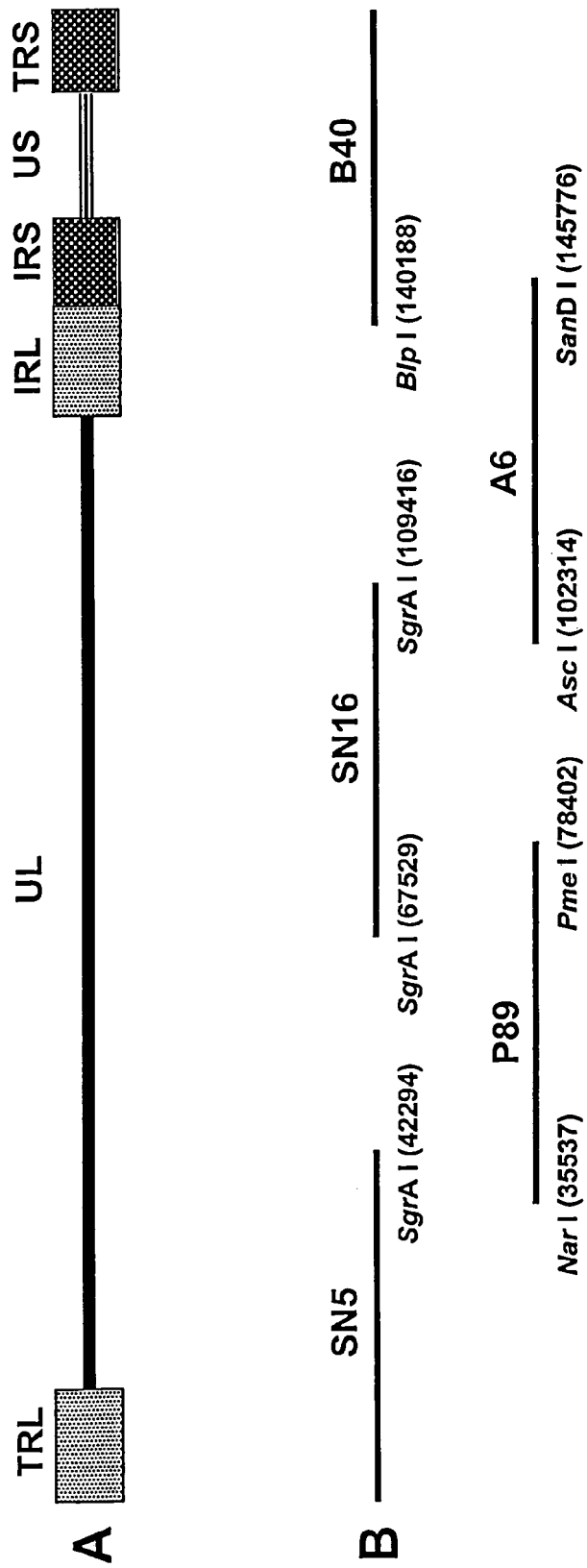
FIG. 1 shows a schematic organization of MDV genome. (A) The genome of MDV consists of unique long ($U_L$) region flanked by inverted repeats, terminal repeat long ($TR_L$), internal repeat long ($IR_L$), and a unique short region ($U_s$) also flanked by two inverted repeats, internal repeat short (Irs and terminal repeat short ($TR_S$). (B) Schematic representation of the overlapping cosmid clones generated to rescue an infectious virus from a very virulent strain of MDV. The restriction sites used to generate the cosmid clones and their positions are indicated. Transfection of SN5, P89, SN16, A6 and B40 into cells in culture resulted in the generation of infectious MDV.
Figure 2:
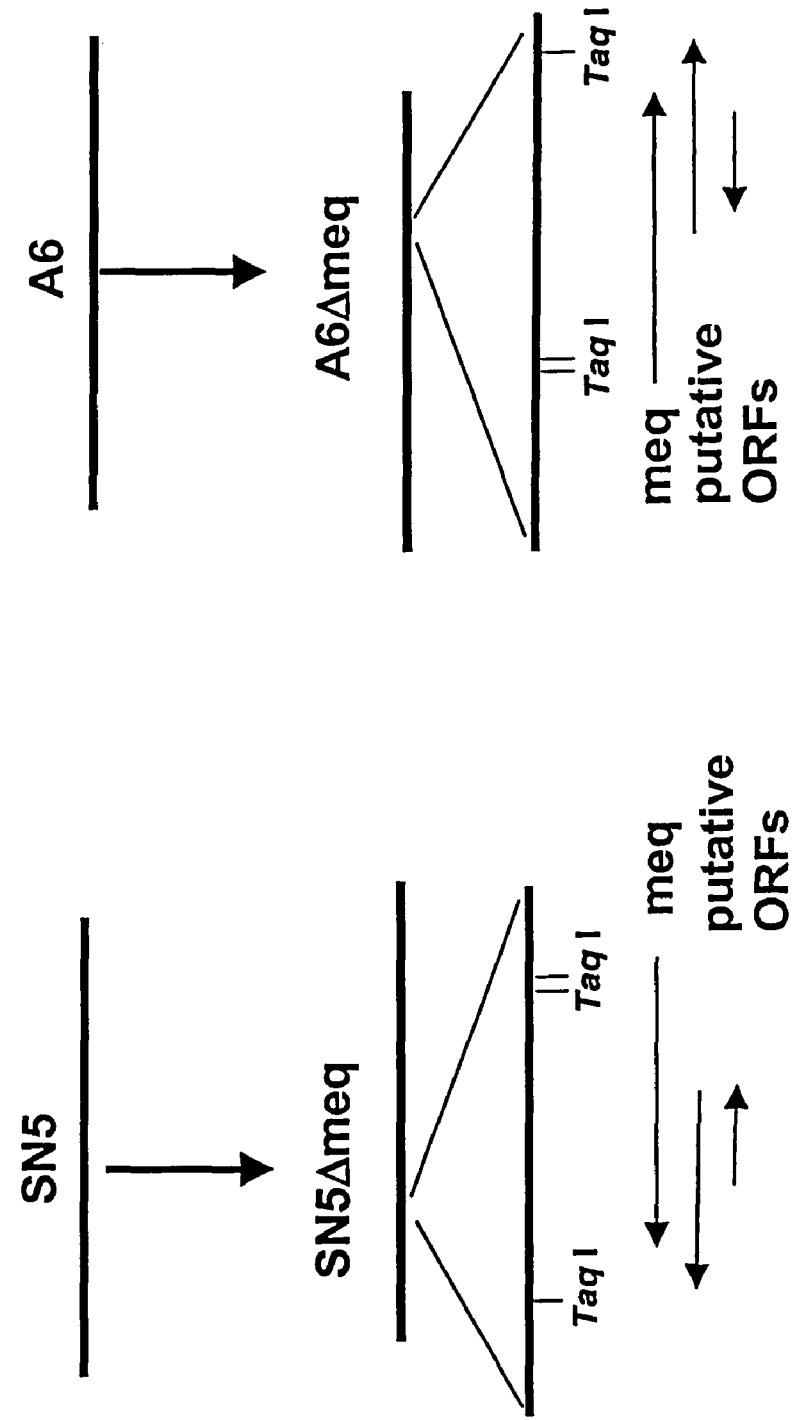
FIG. 2 shows the generation of SN5Δmeq and A6Δmeq cosmid. The complete coding region of the meq gene was deleted from SN5 and A6 cosmids using RecA-assisted restriction endonuclease (RARE) cleavage method.

The meq gene, its encoded protein, and promoter were first identified, characterized, and sequenced by Jones et al. (1992, Proc. Nat'l Acad. Sci., USA, 89:4042-4046, the contents of which are incorporated by reference herein). Meq protein is expressed in all Marek's disease virus transformed cells, and is believed to be an oncogene. The genome of the Marek's disease virus, which is shown in FIG. 1, contains two copies of the meq gene, one in each of the inverted long repeat regions, terminal repeat long ($TR_L$) and internal repeat long ($IR_L$).

Prevention of expression of a functional meq protein by a Marek's disease virus in accordance with this invention may be effected by inactivating both copies of the meq gene or its promoter. The gene or promoter may be inactivated either by insertion of a foreign oligonucleotide or by a deletion. In one embodiment, an oligonucleotide that contains a translational stop codon, may be inserted in the reading frame of the meq gene, such as between the first and last codon of the coding sequence of the gene. Alternatively, the viral agent may have a deletion mutation, such as would be sufficient to cause a frameshift of the reading frame, or a deletion of the entire gene or a sufficient number of nucleotides that any expressed protein is not active as determined by routine testing. In the latter embodiment deletion of the transactivating domain (approximately the ⅔ of the protein from the carboxy end) of the meq gene would be preferred. A variety of techniques are known in the art for performing site-directed mutagenesis, such as disclosed in Sambrook et al. (Molecular Cloning: A Laboratory Manual, second edition, Cold Spring Harbor Laboratory Press, New York, 1989), and are suitable for use herein. However, in the particularly preferred embodiment, both copies of the entire meq gene are deleted from the genome.

In accordance with the preferred embodiment, both copies of the entire meq gene are deleted from the Marek's disease virus genome using overlapping vector clones prepared from any desired strain of Marek's disease virus. The particularly preferred process for the preparation of mutant Marek's disease virus lacking the meq genes is disclosed in detail in the Examples. In summary, to generate overlapping fragments, purified viral DNA may be digested with different restriction-enzyme combinations based on the Marek's disease virus sequences, inserted into a suitable vector, preferably a cosmid, and clones containing the correct restriction pattern for each region of the genome selected for subsequent use. The meq gene may then be deleted from those vectors containing the fragments in which they are mapped, for example, by the RecA-assisted restriction endonuclease (RARE) cleavage method. To generate recombinant Marek's disease virus lacking the meq genes, the vectors containing parental DNA (that portion of the genome which does not contain the meq genes) and the vectors containing mutant DNA (from which the meq gene has been deleted) may be transfected into cells capable of supporting MDV replication (e.g. chicken or duck embryonic fibroblasts).

The particular strain of Marek's disease virus used in the preparation of the vaccine is not critical, and suitable vaccines may be prepared from serotype 1 strains. Moreover, in the preferred embodiment, the vaccine is prepared from very pathogenic serotype 1 strains. Vaccines prepared from such very virulent serotype 1 strains will provide the greatest measure of protection of chickens from against infection by the same or other very virulent serotype 1 strains.

The vaccine of the mutant Marek's disease virus of the invention may be prepared as a cell-free preparation, or in the preferred embodiment, as a cell-associated preparation. A cell-associated vaccine can be prepared directly from in vitro culture of the live viral agents in a suitable cloning medium, such as chicken embryo fibroblasts as described by Witter [U.S. Pat. No. 4,895,718, the contents of which are incorporated by reference herein). Alternatively, to prepare cell-free virus inocula, cells from infected host tissue or cell culture are sonicated or otherwise disrupted as previously described. The cellular debris is removed by centrifugation and the centrifugate recovered as the inoculum. Moreover, while the preferred vaccine is a viable virus, it is also envisioned that the vaccine may be prepared from the killed virus or from immunogenic components separated from, the virus, although such processing would incur significantly greater costs. For example, a subunit vaccine can be prepared by separating from the killed virus one or more purified viral proteins identified as having immunogenic properties.

The viral agent is prepared for administration by formulation in an effective immunization dosage with a pharmaceutically acceptable carrier or diluent, such as physiological saline or tissue culture medium. The expression "effective immunization dosage" is defined as being that amount which will induce immunity in a chicken against challenge by a virulent strain of Marek's disease virus. Immunity is considered as having been induced in a population of chickens when the level of protection for the population is significantly higher than that of an unvaccinated control group. One measure of the level of protection is the protective index (PI), which is calculated as the incidence of Marek's disease in unvaccinated, Marek's disease virus challenged controls minus the incidence of Marek's disease in vaccinated, Marek's disease virus challenged groups, and the difference divided by the percent of Marek's disease in unvaccinated, Marek's disease virus challenged controls, with the result multiplied by 100. Typically, the vaccine will contain at least about 200 PFU (plaque-forming units) of the virus, and preferably between about 2000 and 5000 PFU. The vaccine can be effectively administered anytime after the chicken attains immunocompetence, which is at about the 18th day of incubation (3 days prehatch); but it is normally administered by inoculation within 24-48 hrs after hatching. Alternatively, the viral DNA may be administered as a DNA vaccine as described by Tischer et al. (J. Gen. Virology, 83:2367-2376, 2002, the contents of which are incorporated by reference herein).

Appropriate adjuvants as known in the art may also be included in the vaccine formulation. In many cases, the vaccinal efficacy can be enhanced by combining the meq mutants with other viral agents into bivalent or polyvalent vaccines.

The following examples are intended only to further illustrate the invention and are not intended to limit the scope of the invention which is defined by the claims.

Example 1

Generation of Md5Δmeq Mutant Virus

A mutant of a very virulent strain of a serotype 1 Marek's disease virus, strain Md5, was prepared which lacked both copies of the meq gene.

Both copies of the gene were deleted using a library of overlapping cosmid clones prepared from Md5. To generate the overlapping fragments, purified viral DNA was digested with different restriction enzyme combinations. The restriction enzymes used for cloning the overlapping cosmid DNAs and their locations in the viral genome were as follows: NarI (nucleotide 35537), SgrAI (nucleotides 42294, 67529, and 109416), PmeI (nucleotide 78402), AscI (nucleotide 102314), BlpI (nucleotide 140188), and SanDI (nucleotide 145776) (FIG. 1). After restriction-enzyme digestion, the DNA was blunt-ended with T4 DNA polymerase and ligated to NotI linkers. Ligated DNA was digested with NotI and inserted into NotI-digested SuperCos I cosmid vector (Stratagene). Ligation reactions were packaged with the Gigapack III Gold Packaging Extract (Stratagene) and inserted into HB101 *Escherichia coli* (Life Technologies, Rockville, Md.). To identify bacterial clones containing correct viral DNA inserts, cosmid DNA was isolated, subjected to restriction enzyme digestion with different restriction enzymes, and the patterns obtained were compared with those estimated from the Md5 sequence. Clones with the correct restriction pattern for each region of the genome were selected and used for transfections.

The two copies of the meq gene are present in the A6 and SN5 cosmid clones. The complete coding sequence of the meg gene was deleted from these cosmids by the RecA-assisted restriction endonuclease (RARE) cleavage method described by Ferrin & Camerini-Otero (1991, Science, 254: 5037). Briefly, two oligonucleotides, Meq Taq3' (5' TTT ATG TCA GTA AAT CGA TAA ATA ATG CCT TT 3' positions 5589-5620 and 136000-136031) (SEQ ID No. 1) and Meq Taq5' (5' ACG ATC CGT CCC CCC TCG ATC TTT CTC TCG GGT CG 3' positions 6673-6707 and 134913-134947) (SEQ ID No. 2), located at both ends of the meg gene, were used to protect the Taq I sites (positions 5603, 6672 and 6689 in SN5 cosmid and positions 134928, 134946 and 136014 in A6 cosmid) from methylation. The protected SN5 and A6 cosmids were methylated, using Taq I methylase, digested with Taq I, religated, packaged and introduced into HB101 *E. coli* bacteria. SN5 and A6 cosmid clones in which the meq gene had been deleted, SN5Δmeq and A6Δmeq, were identified by screening for the absence of a 1085 nucleotide pair fragment after digestion with EcoR I.

Transfection of DNA isolated from SN5Δmeq, P89, SN16, A6Δmeq, and B40 cosmid clones, into cells in culture resulted in the generation of a recombinant virus, rMd5Δmeq, lacking the meq gene and two other putative open reading frames which span the meq gene (ORFs). In review, SN5Δmeq, A6Δmeq and parental P89, SN16 and B40 cosmids were digested with Not I to release the viral insert and purified by phenol chloroform extraction and ethanol precipitation prior to transfection. Five hundred ng of each cosmid DNA along with 2 μg of sheared salmon sperm DNA were used to transfected 60-mm dishes containing $1.2 \times 10^6$ duck embryonic fibroblasts (DEF) cells by the calcium phosphate procedure as previously describe (Moriuchi, et al., J. Virol., 66:7303-7308, 1992). Four days after transfection cells, the cells were trypsinized and seeded into 100-mm dish and monitored for cytopathic effects. The virus stocks were subsequently made in DEF cells for further analysis. Typical MDV plaques, resulting from homologous recombination of overlapping DNA fragments, were observed 12-13 days after transfection. Southern blot analysis showed that there was expected deletion of the meq region of rMd5Δmeq. In vitro growth kinetics studies indicated that the recombinant, rMd5Δmeq grew with similar kinetics as parental rMd5.

In order to study the protection capability of the rMd5Δmeq virus, protection studies were conducted in the MD susceptible F1 progeny (15×7) of Avian Disease and Oncology Laboratory line $15I_5$ males and line $7_1$ females. The chickens used in the experiments were derived from breeder hens that were vaccinated with all three serotypes of MDV (Ab-positive). These chickens were randomly sorted into groups and held in modified Horsfall-Bauer isolators for 8 weeks. rMd5Δmeq and control vaccine HVD were administered at day of age and chickens were challenged with a very virulent strain (vv) of MDV, Md5 (Witter, Avian Dis., 41(1): 149-163, January-March, 1997), at day 6 of age (5 days post vaccination). All the chickens that died during the trial or were killed at the end of experiment were examined for typical gross MD lesions. The results are summarized in Table 1.

Mutant Marek's disease virus clone Md5Δmeq (vial nos. RN1804-1828) has been deposited under the provisions of the Budapest Treaty in the American Type Culture Collection (ATCC), 10801 University Blvd., Manassass, Va., 20110-2209, USA, on Jan. 22, 2003, and has been assigned Accession No. ATCC PTA-4944.

It is understood that the foregoing detailed description is given merely by way of illustration and that modifications and variations may be made therein without departing from the spirit and scope of the invention.

TABLE 1

Protection studies of Meq deletion mutant virus rMd5Δmeq (M17-7)

| Virus | Virus Dose | Challenge | MD | PI |
|---|---|---|---|---|
| None | — | — | 0/10 | NA |
| rMd5Δmeq | 2000 | — | 0/17 | NA |
| rMd5 | 2000 | — | 17/17 | NA |
| rMd5Δmeq | 2000 | Md5 | 0/17, 3/17 | 100, 82.4 |
| HVT | 2000 | Md5 | 7/17 | 58.8 |

Chickens: ADOL15X7 line
Antibody status: Maternal antibody positive
Age at challenge: 6 days (5 days post vaccination)
Challenged with 500 plaque forming units of Md5
Termination: 8 weeks post vaccination

We claim:

1. A virus comprising a Marek's disease virus unable to express a functional meq protein, wherein said virus is effective to elicit an immune response in a chicken to Marek's disease virus without causing a significant degree of pathogenicity in said chicken, and further wherein said Marek's disease virus lacks a functional meq gene and both copies of the entire meq gene are deleted.

2. The virus of claim 1 wherein said Marek's disease virus is a serotype 1 Marek's disease virus.

3. The virus of claim 1 wherein said Marek's disease virus is a serotype 1 Marek's disease virus, strain Md5.

4. The virus of claim 1 wherein said Marek's disease virus is viable.

5. The virus of claim 1 wherein said Marek's disease virus is cell associated.

6. A vaccine comprising the virus of claim 1 in an amount effective to elicit an immune response in a chicken to Marek's disease virus and a pharmaceutically acceptable carrier or diluent.

7. A method for protecting a chicken against Marek's disease comprising inoculating said chicken with a vaccine comprising a virus in an amount effective to elicit an immune response in a chicken to Marek's disease virus and a pharmaceutically acceptable carrier or diluent, wherein said virus comprises a Marek's disease virus unable to express a functional meq protein, lacking a functional meq oncogene and both copies of the entire meq oncogene are deleted, further wherein said virus is effective to elicit an immune response in a chicken to Marek's disease virus without causing a significant degree of pathogenicity in said chicken.

* * * * *

SEQUENCE LISTING

```
<160> NUMBER OF SEQ ID NOS: 2

<210> SEQ ID NO 1
<211> LENGTH: 32
<212> TYPE: DNA
<213> ORGANISM: Marek's disease gammaherpesvirus MKT-1

<400> SEQUENCE: 1
tttatgtcag taaatcgata aataatgcct tt                          32

<210> SEQ ID NO 2
<211> LENGTH: 35
<212> TYPE: DNA
<213> ORGANISM: Marek's disease gammaherpesvirus MKT-1

<400> SEQUENCE: 2
acgatccgtc ccccctcgat ctttctctcg ggtcg                       35
```